United States Patent
Tanabe et al.

(10) Patent No.: US 9,072,741 B2
(45) Date of Patent: Jul. 7, 2015

(54) METHODS OF TREATING LIVER FIBROSIS AND PRE-CIRRHOSIS WITH EPIDERMAL GROWTH FACTOR RECEPTOR INHIBITORS

(75) Inventors: Kenneth Tanabe, Brookline, MA (US); Bryan C. Fuchs, Quincy, MA (US)

(73) Assignee: The General Hospital Corporation, Boston, MA (US)

(*) Notice: Subject to any disclaimer, the term of this patent is extended or adjusted under 35 U.S.C. 154(b) by 435 days.

(21) Appl. No.: 12/900,642

(22) Filed: Oct. 8, 2010

(65) Prior Publication Data

US 2011/0086039 A1 Apr. 14, 2011

Related U.S. Application Data

(60) Provisional application No. 61/249,690, filed on Oct. 8, 2009.

(51) Int. Cl.

| | | |
|---|---|---|
| *A01N 43/58* | (2006.01) | |
| *A01N 43/54* | (2006.01) | |
| *A01N 43/00* | (2006.01) | |
| *A61K 31/535* | (2006.01) | |
| *A61K 31/517* | (2006.01) | |
| *A61K 31/5377* | (2006.01) | |

(52) U.S. Cl.
CPC ........... *A61K 31/517* (2013.01); *A61K 31/5377* (2013.01)

(58) Field of Classification Search
CPC ............. A61K 31/5377; A61K 31/506; A61K 31/437; A61K 31/444; A61K 9/0019; A61K 31/4375; A61K 33/00; A61K 31/00; G01N 2800/52; G01N 33/57438; C07D 239/48; C07D 403/04; C07D 401/04
See application file for complete search history.

(56) References Cited

U.S. PATENT DOCUMENTS

| | | | | |
|---|---|---|---|---|
| 6,358,954 | B1* | 3/2002 | Levitzki et al. | 514/250 |
| 7,595,378 | B2* | 9/2009 | van de Winkel et al. | 530/388.1 |
| 2007/0270362 | A1* | 11/2007 | Harlan et al. | 514/44 |
| 2008/0166358 | A1 | 7/2008 | Tung | |
| 2010/0184048 | A1 | 7/2010 | Tanabe et al. | |

FOREIGN PATENT DOCUMENTS

| | | |
|---|---|---|
| WO | 2008/121825 | 10/2008 |
| WO | 2010/045470 | 4/2010 |

OTHER PUBLICATIONS

Bataller et al 2005. J. Clin Invest. 115:209-218.*
Anthony et al., "The morphology of cirrhosis," J. Clin. Pathol., 31:395-414 (1978).
Bataller and Brenner, "Liver fibrosis," J. Clin. Invest., 115:209-218 (2005).
Blanc et al., "Mitotic responsiveness of cultured adult human hepatocytes to epidermal growth factor, transforming growth factor alpha, and human serum," Gastroenterology, 102:1340-1350 (1992).
Borlak et al., "Epidermal growth factor-induced hepatocellular carcinoma: gene expression profiles in precursor lesions, early stage and solitary tumours," Oncogene, 24:1809-18019 (2005).
Chang et al., "Migration of hepatic stellate cells in fibrotic microenvironment of diseased liver model," Hepatobiliary Pancreat. Dis. Int., 7:401-405 (2008).
Ciardiello and Tortora, "A novel approach in the treatment of cancer: targeting the epidermal growth factor receptor," Clin. Cancer Res., 7:2958-2970 (2001).
Fisher and Lakshmanan, "Metabolism and effects of epidermal growth factor and related growth factors in mammals," Endocr. Rev., 11:418-442 (1990).
Francois et al., "Prevention of renal vascular and glomerular fibrosis by epidermal growth factor receptor inhibition," FASEB J., 18:926-928 (2004).
Friedman, "Mechanisms of hepatic fibrogenesis," Gastroenterology, 134:1655-1669 (2008).
Hardie et al., "EGF receptor tyrosine kinase inhibitors diminish transforming growth factor-alpha-induced pulmonary fibrosis," Am. J. Physiol. Lung Cell. Mol. Physiol., 294:L1217-L1225 (2008).
Hoffmann et al., "Proliferation of fetal rat hepatocytes in response to growth factors and hormones in primary culture," J. Cell Physiol., 139:654-662 (1989).
Hoshida et al., "Gene expression in fixed tissues and outcome in hepatocellular carcinoma," N. Engl. J. Med., 359:1995-2004 (2008).
International Search Report and Written Opinion; PCT/US2010/051913; mailed Aug. 11, 2011; (pp. 1-5).
Ishak et al., "Histological grading and staging of chronic hepatitis," J. Hepatol. 22: 696-699 (1995).
Ishii et al., "Gefitinib prevents bleomycin-induced lung fibrosis in mice," Am. J. Respir. Crit. Care Med., 174:550-556 (2006).
Ito et al., "Expression and clinical significance of erb-B receptor family in hepatocellular carcinoma," Br. J. Cancer, 84:1377-1383 (2001).
Jones et al., "Epidermal growth factor secreted from the salivary gland is necessary for liver regeneration," Am. J. Physiol., 268:G872-G878 (1995).
Komuves et al., "Expression of epidermal growth factor and its receptor in cirrhotic liver disease," J. Histochem. Cytochem., 48:821-830 (2000).

(Continued)

*Primary Examiner* — Shulamith H Shafer
(74) *Attorney, Agent, or Firm* — Fish & Richardson P.C.

(57) ABSTRACT

This invention relates generally to a therapeutic use of epidermal growth factor receptor inhibitors to reduce fibrosis, e.g., liver fibrosis, or pre-cirrhosis in a subject.

13 Claims, 8 Drawing Sheets

(56) References Cited

OTHER PUBLICATIONS

Lambotte et al., "Effect of sialoadenectomy and epidermal growth factor administration on liver regeneration after partial hepatectomy," Hepatology, 25:607-612 (1997).

Lee et al., "Expression of ErbB receptor proteins and TGF-alpha during diethylnitrosamine-induced hepatocarcinogenesis in the rat liver," Korean J. Hepatol., 13:70-80 (2007).

Llovet et al., "Hepatocellular carcinoma," Lancet, 362:1907-1917 (2003).

Manning et al., "The protein kinase complement of the human genome," Science 298:1912-1934 (2002) Abstract Only.

Mullhaupt et al., "Liver expression of epidermal growth factor RNA. Rapid increases in immediate-early phase of liver regeneration," J. Biol. Chem., 269:19667-19670 (1994).

Noguchi et al., "Influence of epidermal growth factor on liver regeneration after partial hepatectomy in mice," J. Endocrinol., 128: 425-431 (1991).

Philip et al., "Phase II study of Erlotinib (OSI-774) in patients with advanced hepatocellular cancer," J. Clin. Oncol., 23:6657-6663 (2005).

Robinson et al., "The protein tyrosine kinase family of the human genome," Oncogene 19:5548-5557 (2000) Abstract Only.

Schiffer et al., "Gefitinib, an EGFR Inhibitor, Prevents Hepatocellular Carcinoma Development in the Rat Liver with Cirrhosis," Hepatology 41:307-314 (2005).

Stern et al., "Construction of a novel oncogene based on synthetic sequences encoding epidermal growth factor," Science, 235:321-324 (1987).

Tanabe et al., "Epidermal Growth Factor Gene Functional Polymorphism and the Risk of Hepatocellular Carcinoma in Patients with Cirrhosis," JAMA, 299(1):53-60 (2008).

Thomas et al., "Hepatocellular carcinoma: the need for progress," J. Clin. Oncol., 23:2892-2899 (2005).

Thomas et al., "Phase 2 study of erlotinib in patients with unresectable hepatocellular carcinoma," Cancer, 110:1059-1067 (2007).

Tonjes et al., "Autocrine mitogen IgEGF cooperates with c-myc or with the Hcs locus during hepatocarcinogenesis in transgenic mice," Oncogene, 10:765-768 (1995).

Yamamoto et al., "Inhibitory effect of sialoadenectomy on hepatocellular tumourigenesis in male mice induced by 3'-methyl-4-dimethylaminoazobenzene," Virchows Arch., 425:79-82 (1994).

Yang et al., "Liver Fibrosis: Insights into Migration of Hepatic Stellate Cells in Response to Extracellular Matrix and Growth Factors," Gastroenterology, 124:147-159 (2003).

Zhang et al., "Synergistic inhibition of head and neck tumor growth by green tea (-)-epigallocatechin-3-gallate and EGFR tyrosine kinase inhibitor," Int. J. Cancer, 123(5):1005-1014 (2008).

Zhu et al., "Phase 2 study of cetuximab in patients with advanced hepatocellular carcinoma," Cancer, 110:581-589 (2007).

* cited by examiner

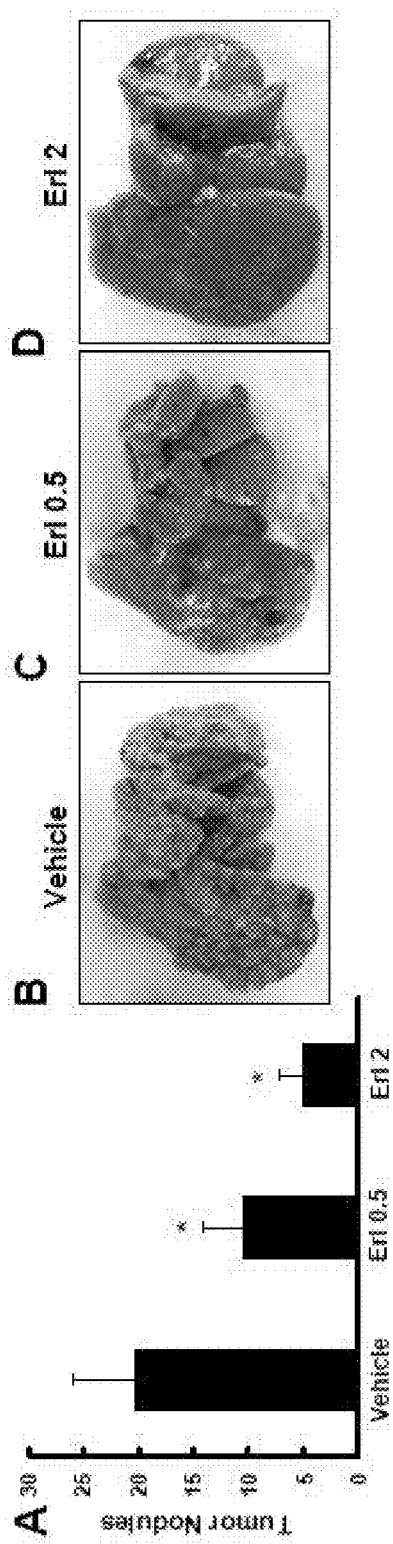
FIGs. 1A-D

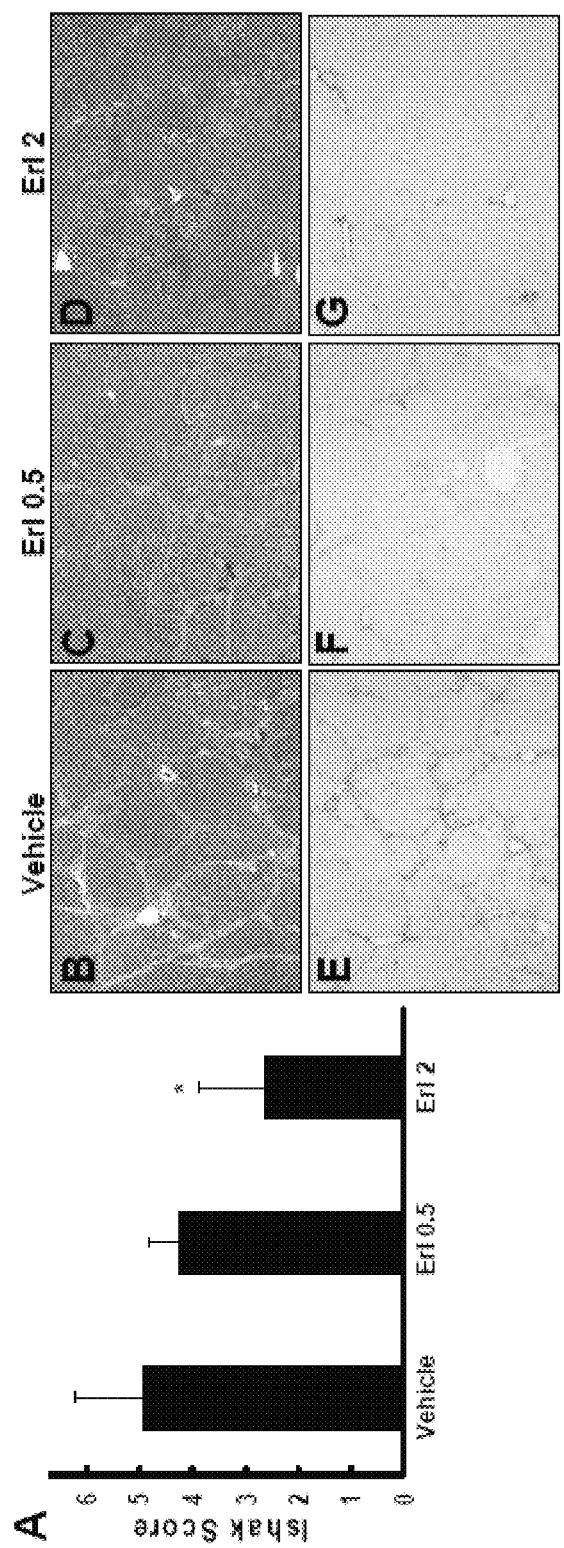
FIGs. 2A-G

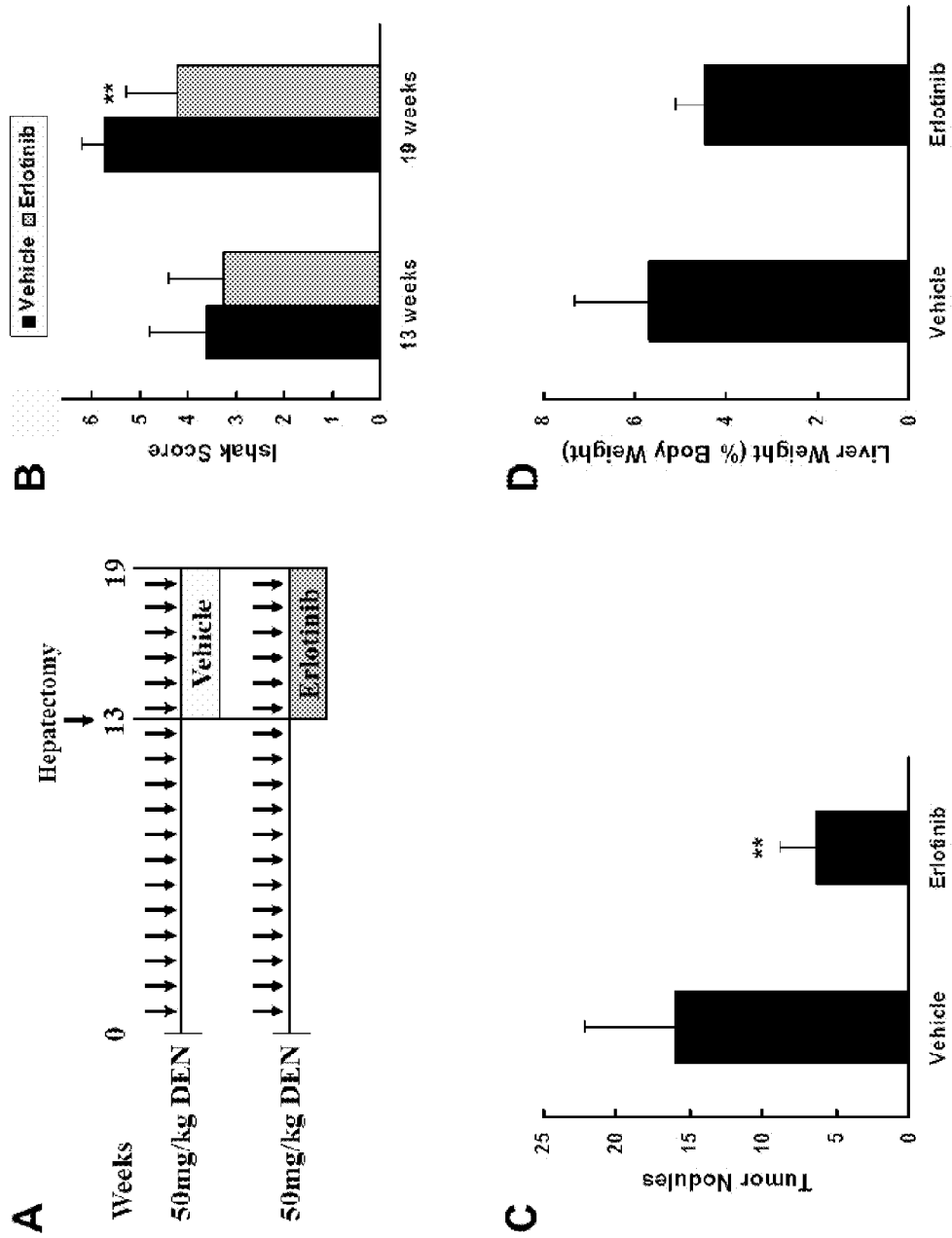
FIGs. 3A-D

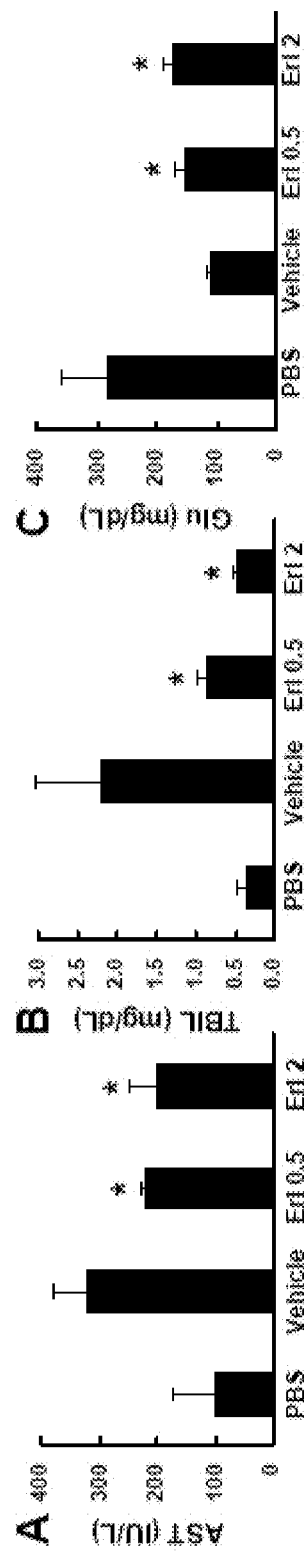
FIGs. 4A-C

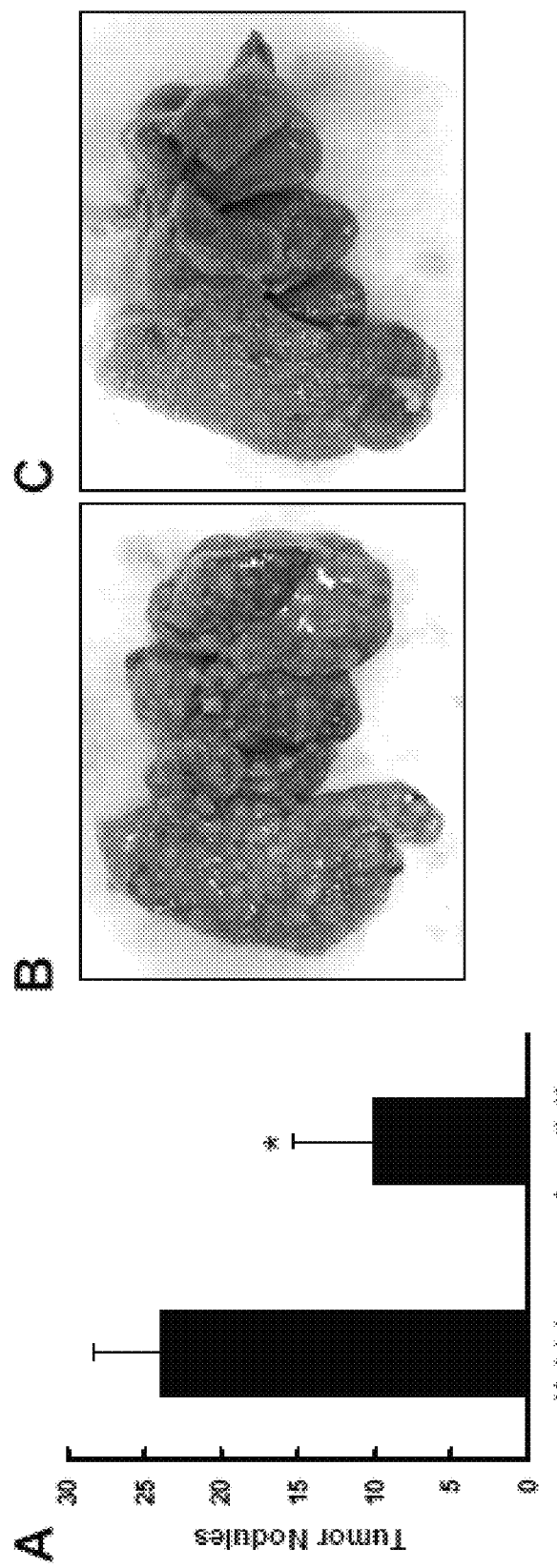
FIGs. 5A-C

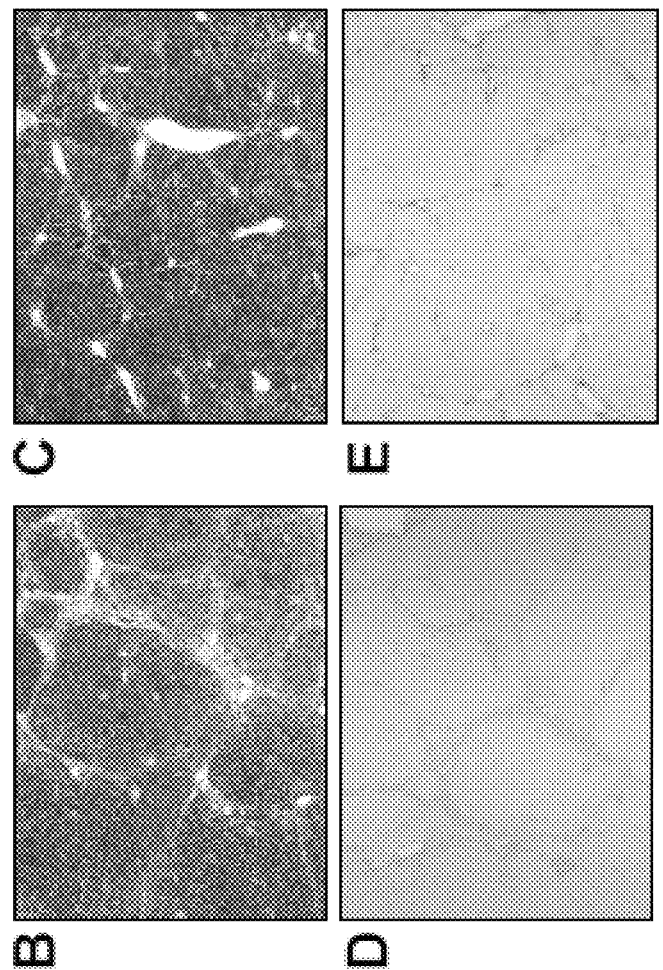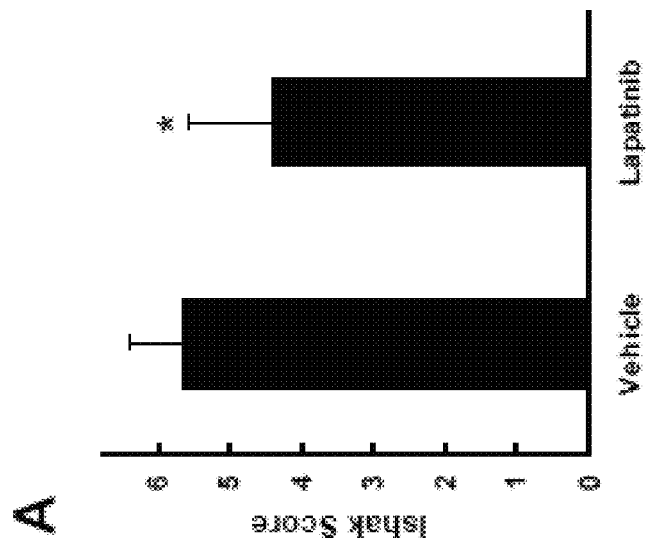
FIGs. 6A-E

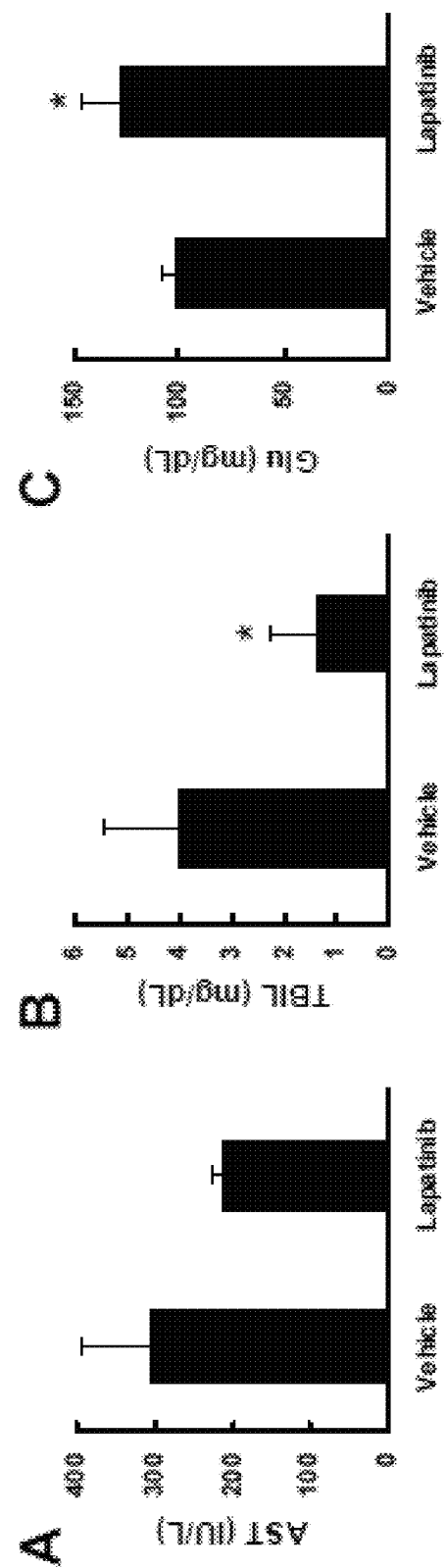
FIGs. 7A-C

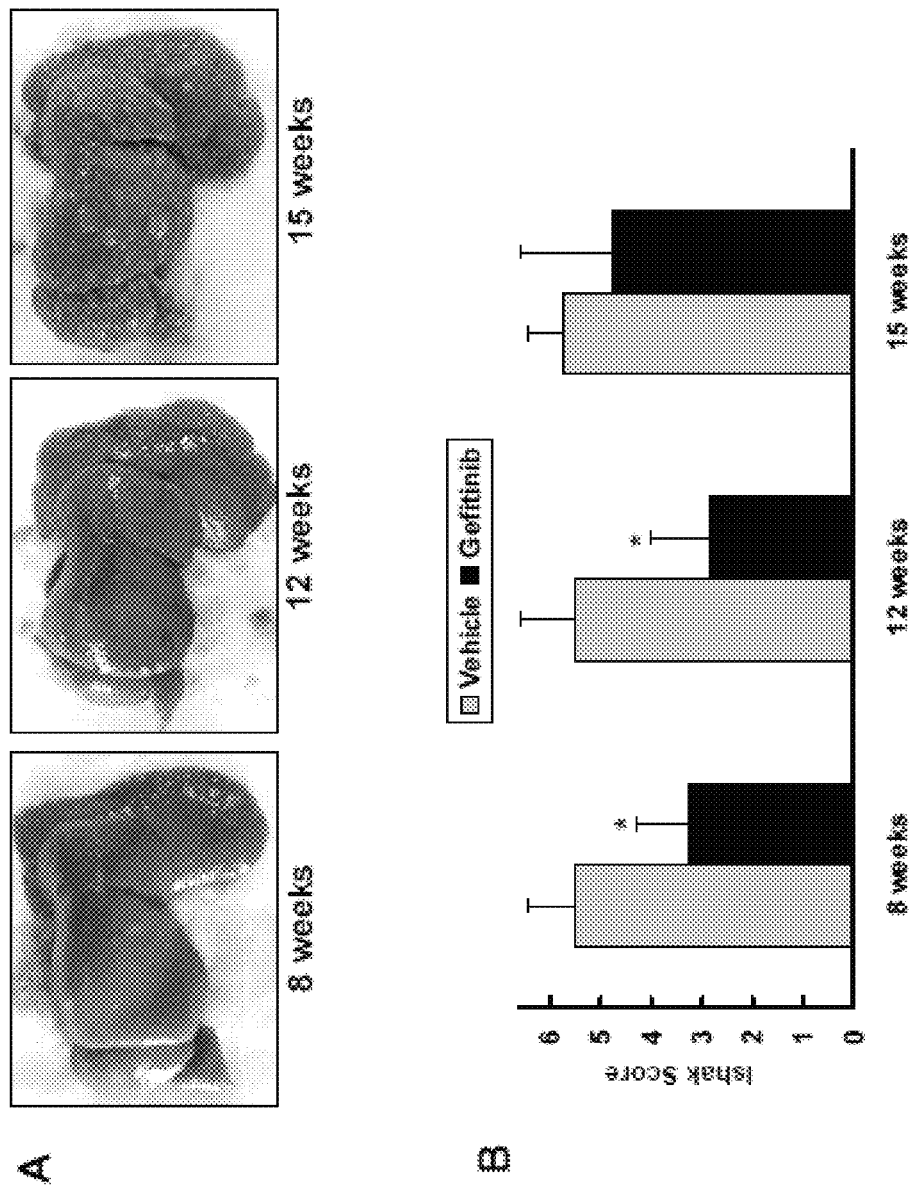
FIGs. 8A-B

METHODS OF TREATING LIVER FIBROSIS AND PRE-CIRRHOSIS WITH EPIDERMAL GROWTH FACTOR RECEPTOR INHIBITORS

CROSS REFERENCE TO RELATED APPLICATIONS

This application claims the benefit of U.S. application Ser. No. 61/249,690, filed on Oct. 8, 2009, the entire contents of which are hereby incorporated by reference.

TECHNICAL FIELD

This disclosure relates to methods of treating fibrosis, e.g., liver fibrosis, and pre-cirrhosis by administering compositions comprising epidermal growth factor receptor inhibitors.

BACKGROUND

The prevalence of chronic liver disease has escalated rapidly worldwide due to the rising number of people inflicted with alcoholism, chronic hepatitis B infection, chronic hepatitis C infection, diabetes, and obesity. During fibrosis and pre-cirrhosis, hepatic stellate cells (HSCs) are activated and deposit fibrous collagen into the space of Disse. As a result, the normal liver architecture is destroyed and normal liver cells, called hepatocytes, can no longer exchange nutrients and wastes with the blood plasma. This ultimately results in cirrhosis, the formation of regenerative nodules of hepatocytes surrounded by fibrous scar tissue. During cirrhosis, the risk of developing hepatocellular carcinoma (HCC) is dramatically elevated as HCC develops in a step-wise progression from regenerative nodules to dysplastic nodules to well-differentiated tumors. Treatment options for HCC are currently ineffective, and as such, HCC is one of the few cancers where the incidence and mortality rates are equal. Therefore, early intervention to reduce fibrosis and pre-cirrhosis and the risk of developing macronodular cirrhosis and HCC would be desirable.

SUMMARY

This invention is based, at least in part, on the discovery that inhibitors of the epidermal growth factor receptor (EGFR) can be used for the treatment of fibrosis, e.g., liver fibrosis, and pre-cirrhosis. Generally, the methods include administering a therapeutically effective amount of an EGFR inhibitor, as known in the art or described herein, e.g., erlotinib, gefitinib, lapatinib, vandetanib, HKI-272 (neratinib), BIBW2992 (Tovok), XL647, and PF00299804, to a subject who is in need of, or who has been determined to be in need of, such treatment. As used in this context, "treatment of fibrosis" means to ameliorate at least one symptom of the disorder associated with fibrosis. "Treatment of pre-cirrhosis" means to ameliorate at least one symptom of the disorder associated with pre-cirrhosis. "Pre-cirrhosis" refers to cirrhosis in the absence of, e.g., prior to the development of, macronodular cirrhosis.

In one aspect, the invention features methods of treating, e.g., reducing severity or progression of, liver fibrosis or pre-cirrhosis in a subject. The methods can include selecting a subject on the basis that they have, or are at risk of developing, liver fibrosis and/or pre-cirrhosis, but do not yet have macronodular cirrhosis or HCC, or a subject with underlying fibrosis or pre-cirrhosis that remains in patients that have had surgery to remove tumorous liver tissue. Selection of a subject can include detecting the presence of liver fibrosis and/or pre-cirrhosis (and/or confirming the absence of macronodular cirrhosis or HCC) by a liver biopsy, a blood test, or imaging tests of the liver. If the results of the test indicate that the subject has fibrosis or pre-cirrhosis, the methods also include administering a therapeutically effective amount of an EGFR inhibitor, e.g., erlotinib, gefitinib, lapatinib, vandetanib, HKI-272 (neratinib), BIBW2992 (Tovok), XL647, and PF00299804, and detecting an effect of the inhibitor on liver fibrosis or pre-cirrhosis in the subject, thereby reducing liver fibrosis or pre-cirrhosis in the subject.

Epidermal growth factor receptor inhibitors include small molecule tyrosine kinase inhibitor that blocks EGFR signaling, e.g., a quinazoline or a monoclonal antibody or antigen binding fragment thereof that binds specifically to the EGFR, e.g., as known in the art and/or described herein. The inhibitors can be administered orally, by injection, e.g., intraperitoneal or intravenous injection, transdermally, or transmucosally.

Epidermal growth factor receptor inhibitors include antibodies such as cetuximab, panitumumab, zalutumumab, nimotuzumab and matuzumab.

In the methods described herein, the amount of epidermal growth factor receptor inhibitor to be administered can be readily determined by one of skill in the art using methods known in the art, and may determine on the specific inhibitor identified. In some embodiments, for example when the inhibitor is a small molecule, daily doses can range from about 0.1 to about 5.0 milligrams per kilogram body weight.

In some embodiments, the methods include a step of evaluating liver function by performing a liver biopsy, a blood test, or a radiological image of the liver. The blood test is used to evaluate liver function by assaying levels of aspartate aminotransferase, alanine aminotransferase, bilirubin, glucose, or hyaluronate.

The invention provides several advantages. The methods disclosed reduce the severity or progression of liver fibrosis and pre-cirrhosis and therefore, inhibit the progression of fibrosis or pre-cirrhosis to macronodular cirrhosis and reduce the risk of developing liver cancers. Currently, no treatment options are effective in decreasing mortality rates of HCC subjects. The methods disclosed reduce the severity of liver fibrosis and pre-cirrhosis and therefore improve liver function, including, but not limited to, production of clotting factors, synthesis of albumin and other proteins, clearance of bilirubin from the bloodstream, and reduction in death of liver cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a bar graph depicting the number of tumor nodules in male Wistar rats receiving weekly intraperitoneal injections of 50 mg/kg diethylnitrosamine (DEN) for 18 weeks and vehicle only (n=16), 0.5 mg/kg erlotinib (Erl 0.5; n=8), or 2 mg/kg erlotinib (Erl 2; n=8) during weeks 12-18.

FIGS. 1B, 1C, and 1D are a series of images showing representative livers from male Wistar rats receiving weekly intraperitoneal injections of DEN (50 mg/kg) for 18 weeks and (B) vehicle only, (C) 0.5 mg/kg erlotinib (Erl 0.5), or (D) 2 mg/kg erlotinib (Erl 2) during weeks 12-18.

FIG. 2A is a bar graph depicting the Ishak score of male Wistar rats receiving weekly intraperitoneal injections of DEN (50 mg/kg) for 18 weeks and vehicle only (n=16), 0.5 mg/kg erlotinib (Erl 0.5; n=8), or 2 mg/kg erlotinib (Erl 2; n=8) during weeks 12-18.

FIGS. 2B-2G are a series of six panels showing representative pictures of Masson's trichome (B-D) and α-SMA stains (E-G) of liver sections from rats receiving weekly intraperitoneal injections of DEN (50 mg/kg) for 18 weeks and (B and E) vehicle only, (C and F) 0.5 mg/kg erlotinib (Erl 0.5), or (D and G) 2 mg/kg erlotinib (Erl 2) during weeks 12-18.

FIGS. 3A-3D shows that erlotinib inhibits fibrogenesis and reverses DEN-induced cirrhosis in rats. FIG. 3A is a scheme of the experiment. Male Wistar rats received weekly intraperitoneal injections of DEN (50 mg/kg) for 18 weeks. After 12 weeks, the rats underwent a survival hepatectomy and a liver biopsy was removed for histology. Rats then received vehicle or erlotinib (2 mg/kg) daily (5 days/week) during weeks 13-18. Rats were sacrificed at 19 weeks after a one-week washout of DEN. FIG. 3B is a bar graph showing Ishak scores from Masson's trichrome stains of liver sections from each animal. p<0.01 compared to vehicle. FIG. 3C is a bar graph depicting the number of tumor nodules that were greater than 5 mm in diameter in rats that received vehicle or erlotinib. p<0.01 compared to vehicle. FIG. 3D is a bar graph showing the weights of livers at the time of sacrifice expressed as percent body weight.

FIGS. 4A, 4B, and 4C are a series of three bar graphs showing the levels of (A) aspartate transaminase (AST), (B) total bilirubin (TBIL), and (C) total glucose (Glu) in serum from rats treated with PBS for 18 weeks or DEN (50 mg/kg) for 18 weeks plus either vehicle, 0.5 mg/kg erlotinib (Erl 0.5), or 2 mg/kg erlotinib (Erl 2) during weeks 12-18. *, significant.

FIG. 5A is a bar graph depicting the number of tumor nodules in male Wistar rats receiving weekly intraperitoneal injections of 50 mg/kg DEN for 18 weeks and vehicle only (n=8) or 18 mg/kg lapatinib (n=8) during weeks 12-18. *, significant.

FIGS. 5B and 5C are a series of images showing representative livers from male Wistar rats receiving weekly intraperitoneal injections of DEN (50 mg/kg) for 18 weeks and (B) vehicle only or (C) 18 mg/kg lapatinib during weeks 12-18.

FIG. 6A is a bar graph depicting the Ishak score of male Wistar rats receiving weekly intraperitoneal injections of DEN (50 mg/kg) for 18 weeks and vehicle only (n=8) or 18 mg/kg lapatinib (n=8) during weeks 12-18. *, significant.

FIGS. 6B-6E are a series of four panels showing representative pictures of Masson's trichome (B-C) and α-SMA stains (D-E) of liver sections from rats receiving weekly intraperitoneal injections of DEN (50 mg/kg) for 18 weeks and (B and D) vehicle only or (C and E) 18 mg/kg lapatinib during weeks 12-18.

FIGS. 7A, 7B, and 7C are a series of three bar graphs showing levels of (A) aspartate transaminase (AST), (B) total bilirubin (TBIL), and (C) total glucose (Glu) in serum from rats treated with DEN (50 mg/kg) for 18 weeks plus either vehicle or 18 mg/kg lapatinib during weeks 12-18. *, significant.

FIG. 8A is a series of images showing representative livers from male Wistar rats receiving weekly intraperitoneal injections of DEN (50 mg/kg) for either 8, 12, or 15 weeks. Macroscopic cirrhosis is not noted until 15 weeks.

FIG. 8B is a bar graph depicting Ishak scores in male Wistar rats receiving weekly intraperitoneal injections of 50 mg/kg DEN for 18 weeks and vehicle only (n=8) or 2 mg/kg gefitnib (n=8) beginning at either 8, 12, or 15 weeks. *, significant.

DETAILED DESCRIPTION

Liver fibrosis is the excessive accumulation of extracellular matrix proteins, including collagen, that occurs in most types of chronic liver diseases. Advanced liver fibrosis often results in liver cirrhosis, increases risk for hepatocellular carcinoma, and frequently requires liver transplantation. Thus, a treatment administered early in the disease process, i.e., to subjects with liver fibrosis or pre-cirrhosis, can result in a reduction in severity of liver cirrhosis and/or reduction in the rate of progression of severity of fibrosis or pre-cirrhosis, and/or reduce the risk of hepatocellular carcinoma, and/or improve liver function and morphology. As demonstrated herein, in subjects with liver fibrosis or pre-cirrhosis, administration of a therapeutically effective amount of an inhibitor of EGFR results in decreased liver disease.

Hepatic Fibrosis and Cirrhosis

Hepatic fibrosis is associated with a process of overly exuberant wound healing, which results in an accumulation of excessive connective tissue in the liver due to a build-up of extracellular matrix overproduction and/or insufficient degradation. In general, the fibrotic process is triggered by chronic injury, especially if there is an inflammatory component. Hepatic fibrosis by itself usually is generally asymptomatic, but can lead to portal hypertension (in which case the scarring distorts hepatic blood flow) or cirrhosis (in which the failure to properly replace destroyed liver cells results in liver dysfunction), which results in widespread distortion of normal hepatic architecture. Cirrhosis is characterized by the presence of regenerative nodules surrounded by dense fibrotic tissue. Symptoms associated with cirrhosis may not develop for years and are often nonspecific (e.g., anorexia, fatigue, weight loss). Late manifestations include portal hypertension, ascites, and, when decompensation occurs, liver failure. A diagnosis of fibrosis or cirrhosis can be confirmed by liver biopsy.

EGF Biology

EGF was first isolated in 1962 (Cohen, J Biol Chem 237: 1555-62, 1962). The EGF gene is transcribed into what is commonly called preproEGF mRNA (Bell et al., Nucleic Acids Res 14:8427-46, 1986), which is translated into a large precursor protein, referred to as proEGF that is ~170 kilodaltons (KDa) after glycosylation (Marti et al., Hepatology 9:126-38, 1989). Thus, EGF is synthesized as a nondiffusible, glycosylated membrane-associated precursor, which is exposed at the cell surface. Proteolytic cleavage releases the proEGF in a process known as ectodomain shedding (Le Gall et al., J Biol Chem 278:45255-68, 2003), which is mediated by a metalloproteinase of the a disintegrin and metalloprotease (ADAM) family. Ectodomain shedding of EGF has been shown to be mediated by both ADAM10 (Sahin et al., J Cell Biol 164:769-79, 2004) and ADAM17 (Chen et al., Am J Physiol Cell Physiol 291:C946-56, 2006). Additional proteases present in the extracellular space/fluid can further cleave proEGF. The isoforms detected range in size depending on the source, with the 6 KDa form being referred to as mature EGF. All the isoforms have been reported to be biologically active, although the smaller isoforms bind EGF receptor (EGFR) with greater affinity. Once EGF binds EGFR, EGFR undergoes a transition from an inactive monomer to an active homodimer. The homodimer stimulates its intrinsic intracellular protein-tyrosine kinase activity and several signaling pathways can be initiated, including phosphoinositide 3-kinase (PI3K)/AKT, janus kinase (JAK)/signal transducers and activator of transcription (STAT) and several mitogen-activated protein kinases (MAPKs), including extracellular signal-regulated kinase (ERK) and c-jun N-terminal kinase (JNK) (Yarden and Sliwkowski, Nat Rev Mol Cell Biol 2:127-37, 2001; Yarden and Shilo, Cell 131: 1018, 2007). Upon binding EGFR, EGF is internalized within the cell.

EGF and Cancer

Since its discovery, EGF has been shown to have many biological functions, including stimulating the proliferation and differentiation of epidermal and epithelial tissues (Carpenter and Cohen, Annu Rev Biochem 48:193-216, 1979; Fisher and Lakshmanan, Endocr Rev 11:418-42, 1990). EGF also has important roles in tumorigenesis as it enhances both chemical carcinogenesis and viral transformation (Stoscheck and King, Cancer Res 46:1030-7, 1986), as well as the in vitro growth of human epithelial and mesenchymal-derived tumors (Singletary et al., Cancer Res 47:403-6, 1987). Further, overexpression of EGFR (c-ErbB1, HER1), is a common event in neoplastic transformation (Herbst and Shin, Cancer 94:1593-611, 2002) and for this reason, EGFR has emerged as an important chemotherapeutic target (Ciardiello and Tortora, Clin Cancer Res 7:2958-70, 2001; Mendelsohn and Baselga, J Clin Oncol 21:2787-99, 2003; Roskoski, Biochem Biophys Res Commun 319:1-11, 2004).

EGF and the Liver

EGF is a known mitogen for adult (Blanc et al., Gastroenterology 102:1340-50, 1992) and fetal hepatocytes (Hoffmann et al., J Cell Physiol 139:654-62, 1989) grown in culture. EGF transcription is induced during the immediate-early phase of liver regeneration (Mullhaupt et al., J Biol Chem 269:19667-70, 1994) where it plays a vital role in hepatocyte proliferation. In rodents, the main source of EGF is the salivary glands (Fisher and Lakshmanan, Endocr Rev 11:418-42, 1990), and removal of these glands lowers plasma (Noguchi et al., J Endocrinol 128: 425-31, 1991) and serum (Yamamoto et al., Virchows Arch 425:79-82, 1994) levels of EGF. Furthermore, sialoadenectomized rats (Lambotte et al., Hepatology 25:607-12, 1997; Jones et al., Am J Physiol 268: G872-8, 1995) and mice (Noguchi et al., J Endocrinol 128: 425-31, 1991) have impaired liver regeneration after partial hepatectomy, which can be restored to normal with exogenous addition of EGF (Lambotte et al., Hepatology 25:607-12, 1997; Jones et al., Am J Physiol 268:G872-8, 1995; Noguchi et al., J Endocrinol 128: 425-31, 1991). Additional studies demonstrated that sialoadenectomized mice developed fewer HCC nodules in response to the carcinogen, 3'-methyl-4-dimethylaminoazobenzene (Yamamoto et al., Virchows Arch 425:79-82, 1994). Therefore, increased expression of EGF during liver regeneration may be beneficial for the regenerative process, but could also lead to an increased risk of cancer.

EGF and HCC

Overexpression of EGF in the liver induces transformation to HCC in animal models. For example, Stern et al. constructed a plasmid to express a secretable form of human EGF termed IgEGF (Stern et al., Science 235:321-4, 1987). When IgEGF expression was targeted to the liver by the addition of an albumin promoter/enhancer element, transgenic mice expressing this transgene at high levels developed HCC and died within 7 months, whereas lower expressing mice developed HCC within 8-13 months (Tonjes et al., Oncogene 10:765-8, 1995; Borlak et al., Oncogene 24:1809-19, 2005). This study suggested that a dose-response exists between levels of EGF and risk of HCC.

EGF Expression and Chronic Liver Disease

Chronic liver injury causes fibrosis or pre-cirrhosis, ultimately resulting in cirrhosis, and increases risk for HCC. Liver synthesis of EGF is marginal; however its expression has been reported to increase in cirrhotic livers (Komuves et al., J Histochem Cytochem 48:821-30, 2000). Consistent with this, a recent report has shown that EGF is part of a gene-expression signature in the surrounding nontumoral liver tissue that is associated with recurrence and poor survival in HCC patients who had undergone potentially curative resection (Hoshida et al., N Engl J Med 359:1995-2004, 2008). Chronic liver injury causes a local population of endothelial cells, macrophages (Kupffer cells), and hepatic stellate cells to become active and secrete several cytokines and growth factors into the liver milieu, which stimulate the surrounding hepatocytes (Bataller and Brenner, J Clin Invest 115:209-18, 2005).

Known EGFR-Targeted Therapies

EGFR has emerged as a promising chemotherapeutic target as it is overexpressed in a wide range of cancers and plays important roles in cell growth and survival (Ciardiello and Tortora, Clin Cancer Res 7:2958-70, 2001). Several drugs that target EGFR have emerged including the small-molecule tyrosine kinase inhibitors, e.g., the quinazolines, e.g., erlotinib (4-Quinazolinamine, N-(3-ethynylphenyl)-6,7-bis(2-methoxyethoxy); brand name Tarceva®, from OSI Pharmaceuticals); gefitinib (4-Quinazolinamine, N-(3-chloro-4-fluorophenyl)-7-methoxy-6-(3-(4-morpholinyl)propoxy); brand name Iressa®, from AstraZeneca); lapatinib (4-Quinazolinamine, N-(3-chloro-4-((3-fluorophenyl)methoxy)phenyl)-6-(5-(((2-(methylsulfonyl)ethyl)amino)methyl)-2-furanyl); brand name Tykerb®, from GlaxoSmithKline); vandetanib (4-Quninazolinamine, N-(4-bromo-2-fluorophenyl)-6-methoxy-7-((1-methyl-4-piperidinyl) methoxy); brand name Zactima®, from AstraZeneca); HKI-272 (neratinib, (2E)-N-(4-((3-chloro-4-((pyridin-2-yl) methoxy)phenyl)amino)-3-cyano-7-ethoxyquinolin-6-yl)-4-(dimethylamino)but-2-enamide, from Wyeth), BIBW2992 (2-Butenamide, N-(4-((3-chloro-4-fluorophenyl)amino)-7-(((3S)-tetrahydro-3-furanyl)oxy)-6-quinazolinyl)-4-(dimethylamino); brand name Tovok®, from Boehringer Ingelheim), XL647 (from Exelixis); and PF00299804 (from Pfizer); as well as monoclonal antibodies, or antigen-binding fragments thereof, that selectively bind to the EGFR, e.g., cetuximab (Erbitux®), panitumumab (Vectibix®), zalutumumab (HuMax-EGFr, from GenMab), nimotuzumab (from YM Biosciences), and matuzumab (Merck Serono/Takeda). (Mendelsohn and Baselga, J Clin Oncol 21:2787-99, 2003). Previous reports document EGFR overexpression in HCC (Ito et al., Br J Cancer 84:1377-83, 2001). Unfortunately, in recent clinical trials, erlotinib improved disease control in only a minority of advanced HCC patients (Philip et al., J Clin Oncol 23:6657-63, 2005; Thomas et al., Cancer 110:1059-67, 2007) and no responses were seen after treatment with cetuximab (Zhu et al., Cancer 110:581-9, 2007). See also US 2008/0166358.

Erlotinib Chemoprevention of HCC

Given the lack of successful treatment options for HCC, chemoprevention in high-risk patients has been proposed as an alternative strategy (Llovet et al., Lancet 362:1907-17, 2003). Even though EGFR inhibition is not effective for chemotherapy, the data presented herein indicate that it is likely to be a good chemoprevention strategy. The diethylnitrosamine (DEN)-induced rat model of sequential cirrhosis and HCC has emerged as a promising tool for not only studying the course of chronic liver disease but also for testing putative chemopreventive agents as it better resembles disease progression in humans (Lee et al., Korean J Hepatol 13:70-80, 2007; Schiffer et al., Hepatology 41:307-14, 2005). In this model, DEN induces liver cirrhosis after 12 weeks and HCC at approximately 18 weeks allowing ample opportunity for preventative intervention. Using this model, erlotinib was shown to decrease tumor formation when administered as a chemopreventive agent during weeks 12-18 (see Examples 1-2, herein). Similar results have also been reported for gefitinib (Schiffer et al., Hepatology 41:307-14, 2005).

Erlotinib Inhibits Fibrogenesis

As shown herein, erlotinib inhibits fibrogenesis in the DEN-induced rat model. Further, erlotinib reduced hepatotoxicity as assessed by decreased serum levels of aspartate transaminase and improved liver function as assessed by decreased serum levels of bilirubin and increased serum levels of glucose. As one theory, not meant to be limiting, these effects may be explained by the ability of erlotinib to prevent the activation of hepatic stellate cells. This is consistent with previous reports showing that EGF can activate hepatic stellate cells (Yang et al., Gastroenterology 124:147-59, 2003; Chang et al., Hepatobiliary Pancreat Dis Int 7:401-5, 2008). EGFR-targeted therapies have been shown to reduce pulmonary fibrosis (Ishii et al., Am J Respir Crit Care Med 174:550-6, 2006; Hardie et al., Am J Physiol Lung Cell Mol Physiol 294:L1217-25, 2008) and renal fibrosis (Francois et al., FASEB J 18:926-8, 2004). However, this is the first report that EGFR-targeted therapies can reduce or inhibit liver fibrosis and pre-cirrhosis.

Subjects to be Treated

In one aspect of the methods described herein, a subject is selected on the basis that they have, or are at risk of developing, fibrosis or pre-cirrhosis. Many types of fibrosis can be treated, including liver fibrosis, cystic fibrosis of the pancreas and lungs, idiopathic pulmonary fibrosis of the lung, endomyocardial fibrosis, mediastinal fibrosis, myelofibrosis, retroperitoneal fibrosis, progressive massive fibrosis, injection fibrosis, and nephrogenic systemic fibrosis. As used herein, "pre-cirrhosis" refers to a cirrhotic condition characterized by the absence of macronodular cirrhosis, e.g., a stage of cirrhosis prior to the development of macronodular cirrhosis.

A subject that has, or is at risk of developing, liver fibrosis or pre-cirrhosis is can be diagnosed or identified by one of skill in the art based on the totality of the evidence, including the presence of one or more symptoms of the condition. Symptoms of liver fibrosis or pre-cirrhosis vary greatly and are well-known to those of skill in the art and may include, without limitation, shrunken liver, liver pain, jaundice, jaundice-like symptoms (e.g., yellow skin, yellow eyes), abnormal liver function tests, abdominal pain, kidney pain, kidney failure, abnormal nerve function, gallstones, hair loss, itchy skin, muscle loss, poor appetite, weight loss, portal hypertension, redness of palms, spider-like veins in the skin, enlarged veins around the esophagus or stomach (varices), small testicles (atrophy), enlargement of the spleen, low platelet count, enlargement of the breasts (gynecomastia), and salivary gland enlargement in cheeks.

Liver fibrosis and pre-cirrhosis can be further diagnosed by, for example, a biopsy, serum aspartate aminotransferase, bilirubin, glucose, hyaluronate (Patel et al., J Gastroenterol Hepatol 18:253-257, 2003), procollagen III N-peptide (Guechot et al., Clin Chem 42:558-563, 1996), laminin (Pilette et al., J Hepatol 28:439-446, 1998), type IV collagen (Castera et al., J Hepatol32:412-418, 2000), matrix metalloproteases (Murawaki et al., J Gastroenterol Hepatol 14:138-145, 1999), tissue inhibitory metalloprotease-1 (Boeker et al., Clin Chim Acta 316:71-81, 2002), transforming growth factor-beta (Nelson et al., J Viral Hepat 4:29-35, 1997), YKL-40 (Johansen et al., J Hepatol 32:911-920, 2000), prothrombin index (Oberti et al., Gastroenterology 113:1609-1616, 1997), gamma-globulin, platelet count (Pohl et al., Am J Gastroenterol 96:3142-3146, 2001), aspartate aminotransferase (AST)/alanine aminotransferase (ALT) ratio (Imperiale et al, Am J Gastroenterol 95:2328-2332, 2000), and Fibrolndex (Koda et al., Hepatology 45:297-306, 2007). Imaging studies can be used to diagnose fibrosis or pre-cirrhosis, e.g., x-rays, magnetic resonance imaging, CT scan, or magnetic resonance elastography of the liver. Such methods can be used to rule out the presence of macronodular cirrhosis. A subject that is "at risk of developing liver fibrosis or pre-cirrhosis" is one that has a predisposition to develop liver fibrosis or pre-cirrhosis (e.g., a genetic predisposition to develop liver fibrosis or pre-cirrhosis such as a mutation in a gene implicated in hepatic fibrogenesis, e.g., IL-10, TNF-$\alpha$, IL-4R, TGF-$\beta$1, AT-II, CTLA-4, or MMP-3 (Friedman, Gastroenterology 134:1655-1669 2008), or that has been exposed to conditions that can result in liver fibrosis or pre-cirrhosis. Thus, a subject that is "at risk of developing liver fibrosis or pre-cirrhosis" can be a subject who has one or more of alcoholism, chronic hepatitis B infection, chronic hepatitis C infection, diabetes, or obesity. In some embodiments, subjects treated using the methods described herein have fibrosis, but do not have macronodular cirrhosis or HCC. In some embodiments, subjects treated using the methods described herein have pre-cirrhosis, but do not have macronodular cirrhosis or HCC.

The present methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

Administration of Compounds

Systemic administration of a therapeutic EGFR inhibiting compound as described herein can be parenteral, e.g., by infusion (e.g., intravenous) or injection (e.g., intraperitoneal), transmucosal, or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. In some embodiments, the compounds are delivered directly to the liver, e.g., via infusion into the common hepatic artery, the celiac artery, or the portal vein. EGFR inhibitors can also be administered orally.

Dosage, toxicity and therapeutic efficacy of the compounds can be determined, e.g., by known pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect, i.e., a reduction in fibrosis or pre-cirrhosis. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The following are examples of the practice of the invention.

EXAMPLES

The invention is further described in the following examples, which do not limit the scope of the invention described in the claims.

Example 1

Erlotinib Reduces Fibrogenesis and Inhibits Hepatic Stellate Cell Activation

Erlotinib is a drug used to treat non-small cell lung cancer and pancreatic cancer. Erlotinib specifically targets the EGFR, which is highly expressed and occasionally mutated in various forms of cancer, by binding to the adenosine triphosphate (ATP) binding site of the receptor (Raymond et al., Drugs 60 Suppl 1:15-23, 2000). To investigate erlotinib as a chemoprevention strategy for liver fibrogenesis, male Wistar rats were given a weekly intraperitoneal injection of 50 mg/kg DEN to induce cirrhosis and HCC (Lee et al., Korean J Hepatol 13:70-80, 2007). Erlotinib was administered by intraperitoneal injection daily (5× a week) during weeks 12-18 at a dose of 2 mg/kg, which is equivalent to chemotherapeutic dosing regimens in humans. Erlotinib dramatically decreased tumor formation by 75% under these conditions (FIG. 1A). In a separate study, the dose of erlotinib was lowered to 0.5 mg/kg. In this second study, erlotinib was shown to inhibit tumor formation by 49% (FIG. 1A).

The livers from DEN-induced rats treated with erlotinib (FIGS. 1C and 1D) not only exhibited less tumors, but also appeared less cirrhotic compared to vehicle controls (FIG. 1B). Repeated injury to the liver causes damage to hepatocytes and activates resident macrophages called Kupffer cells. Damaged hepatocytes and activated Kupffer cells secrete cytokines and growth factors into the liver milieu, which activate hepatic stellate cells (Friedman, Gastroenterology 134:1655-69, 2008). Normally, hepatic stellate cells are quiescent and store vitamin A and fat. Upon activation, they differentiate into a myofibroblast-phenotype and express α-smooth muscle actin (α-SMA) (Friedman, Gastroenterology 134:1655-69, 2008). Activated hepatic stellate cells deposit fibrous collagen into the space of Disse acutely causing fibrosis and chronically causing cirrhosis. The degree of liver disease (fibrosis versus cirrhosis) is pathologically assessed through trichrome staining of collagen by the method of Ishak (Mod Pathol 7:690-713, 1994).

In early stages of liver fibrosis, collagen deposition is localized around the portal tracts (Ishak score 1 or 2), but it bridges between portal tracts at later stages of fibrosis (Ishak score 3 or 4) and ultimately forms nodules around regenerating hepatocytes during cirrhosis (Ishak score 5 or 6). Although there is some heterogeneity in this model, intraperitoneal administration of DEN causes, on average, an Ishak score 0.8 (range 0-2) fibrosis after 8 weeks, an Ishak score 4.1 (range 3-6) fibrosis/cirrhosis after 12 weeks, and an Ishak score 5.1 (range 4-6) cirrhosis after 18 weeks. Consistent with this, hepatic stellate cell activation increases over time after DEN administration as assessed by α-SMA staining.

Remarkably, erlotinib inhibited fibrogenesis. Rats that received 2 mg/kg erlotinib significantly regressed to an average Ishak score 2.6 fibrosis compared to rats that received vehicle solution, which had on average, an Ishak score 4.9 fibrosis/cirrhosis (FIG. 2A). Rats that received 0.5 mg/kg erlotinib also had a lower Ishak score 4.3 fibrosis/cirrhosis. The range for 16 vehicle animals was 2-6 with a mode of 6 as illustrated in FIG. 2B. By comparison, the range for 0.5 mg/kg erlotinib was 3-6 with a mode of 4 as illustrated in FIG. 2C, while the range for 2 mg/kg erlotinib was 1-4 with a mode of 2 as illustrated in FIG. 2D. To further examine the effects of erlotinib on liver fibrosis, α-SMA staining was performed for activated hepatic stellate cells. Compared to vehicle controls, erlotinib dramatically decreased the activation of hepatic stellate cells in a dose-dependent fashion (FIGS. 2E-G).

Example 2

DEN-Treated Rats that Receive Erlotinib as a Preventive Agent Between Weeks 13 and 18 have Reduced Levels of Fibrosis and Cirrhosis Interestingly, it also appeared that erlotinib may be able to reverse fibrosis and cirrhosis in DEN-treated rats. To further examine the ability of erlotinib to reverse fibrosis and cirrhosis, liver biopsies were performed on DEN-treated rats before and after they received erlotinib (FIG. 3A) to determine disease progression within the same animal. Similar to the study described in Example 1, erlotinib-treated rats had significantly less fibrosis and cirrhosis (FIG. 3B) as well as a significant decrease in tumorigenesis (FIG. 3C), which is consistent with the observed decrease in liver weight (FIG. 3D). Further, erlotinib reversed disease progression in two out of eight animals (Table 1).

TABLE 1

Ishak scores from 16 DEN-treated rats, eight of which
received vehicle only and eight others that were
treated with erlotinib between weeks 13 to 18.

|  | Ishak 13 weeks | Ishak 19 weeks | Change |
|---|---|---|---|
| Vehicle | | | |
| DEN 123 | 2 | 5 | +3 |
| DEN 129 | 4 | 6 | +2 |
| DEN 130 | 5 | 6 | +1 |
| DEN 131 | 4 | 6 | +2 |
| DEN 132 | 2 | 5 | +3 |
| DEN 133 | 3 | 6 | +3 |
| DEN 134 | 5 | 6 | +1 |
| DEN 135 | 4 | 6 | +2 |
| AVERAGE | 3.6 | 5.8 | +2.2 |
| Erlotinib | | | |
| DEN 122 | 3 | 6 | +3 |
| DEN 125 | 3 | 5 | +2 |
| DEN 126 | 2 | 4 | +2 |
| DEN 127 | 5 | 3 | −2 |
| DEN 136 | 5 | 4 | −1 |
| DEN 137 | 2 | 3 | +1 |
| DEN 138 | 3 | 4 | +1 |
| DEN 139 | 3 | 5 | +2 |
| AVERAGE | 3.3 | 4.3* | +1 |

Example 3

Erlotinib Reduces Hepatotoxicity and Improves Liver Function

During fibrosis, hepatic stellate cells are activated and deposit fibrous collagen into the space of Disse, the area between the hepatocytes and the sinusoid containing blood plasma. The deposition of collagen inhibits the normal exchange of nutrients and wastes between the hepatocytes and plasma resulting in hepatotoxicity and liver failure. The degree of liver toxicity and failure can be assessed by measuring several proteins or a carbohydrate present in the serum. For example, aspartate aminotransferase (AST) is an enzyme present in hepatocytes that is released into the serum when hepatocytes die. Bilirubin (TBIL) is the breakdown product of heme and its levels become elevated in the serum if hepatocytes cannot properly metabolize it. Finally, liver failure will result in lower levels of glucose (Glu) production causing serum Glu levels to drop.

The levels of AST, TBIL, and Glu were assayed in serum from rats treated with erlotinib. Male Wistar rats (n=4) were treated with PBS for 18 weeks or a weekly intraperitoneal injection of 50 mg/kg DEN for 18 weeks plus either vehicle, 0.5 mg/kg erlotinib (Erl 0.5), or 2 mg/kg erlotinib (Erl 2) between weeks 12 and 18. Whole blood was isolated from the rats and allowed to clot for 2 hours at room temperature. The blood was then spun at 2,000 rpm for 10 minutes and serum (top layer) was isolated. Liver function tests were performed on serum from the rats. In the current model, intraperitoneal administration of DEN causes both hepatotoxicity and liver failure to increase over time as assessed by these three markers. However, compared to vehicle controls, erlotinib reduced the degree of hepatotoxicity and liver failure in a dose-dependent fashion. Specifically, erlotinib decreased serum levels of AST and TBIL and increased serum levels of Glu (FIGS. 4A-C).

Example 4

Lapatinib Reduces Fibrogenesis and Inhibits Hepatic Stellate Cell Activation

To investigate lapatinib as a chemoprevention strategy for liver fibrogenesis, male Wistar rats were given a weekly intraperitoneal injection of 50 mg/kg DEN to induce cirrhosis and HCC (Lee et al., Korean J Hepatol 13:70-80, 2007). Lapatinib was administered by intraperitoneal injection daily (5× a week) during weeks 12-18 at a dose of 18 mg/kg. Lapatinib dramatically decreased tumor formation by greater than 50% under these conditions (FIG. 5A). The livers from DEN-induced rats treated with lapatinib (FIG. 5C) not only exhibited less tumors, but also appeared less cirrhotic compared to vehicle controls (FIG. 5B).

Similar to erlotinib, lapatinib inhibited fibrogenesis. Rats that received 18 mg/kg lapatinib significantly regressed to an average Ishak score 4.3 fibrosis compared to rats that received vehicle solution, which had on average, an Ishak score 5.6 fibrosis/cirrhosis (FIG. 6A), as shown by Masson's trichrome staining of liver sections from rats receiving weekly intraperitoneal injections of DEN (50 mg/kg) for 18 weeks and (FIG. 6B) vehicle only or (FIG. 6C) 18 mg/kg lapatinib during weeks 12-18. To further examine the effects of lapatinib on liver fibrosis, α-SMA staining was performed for activated hepatic stellate cells. Compared to vehicle controls, lapatinib dramatically decreased the activation of hepatic stellate cells in a dose-dependent fashion (FIGS. 6D-E).

Example 5

Lapatinib Reduces Hepatotoxicity and Improves Liver Function

Levels of AST, TBIL, and Glu were assayed in serum from rats treated with lapatinib. Male Wistar rats (n=4) were treated with PBS for 18 weeks or a weekly intraperitoneal injection of 50 mg/kg DEN for 18 weeks plus either vehicle or 18 mg/kg lapatinib between weeks 12 and 18. Whole blood was isolated from the rats and allowed to clot for 2 hours at room temperature. The blood was then spun at 2,000 rpm for 10 minutes and serum (top layer) was isolated. Liver function tests were performed on serum from the rats. In the current model, intraperitoneal administration of DEN causes both hepatotoxicity and liver failure to increase over time as assessed by these three markers. However, compared to vehicle controls, lapatinib reduced the degree of hepatotoxicity and liver failure. Specifically, lapatinib decreased serum levels of AST and TBIL and increased serum levels of Glu (FIGS. 7A-C).

Example 6

Male Wistar rats received weekly intraperitoneal injections of DEN (50 mg/kg) for 16 weeks. Rats received vehicle control or gefitinib (2 mg/kg) daily beginning at either 8, 12, or 15 weeks and lasting until 18 weeks. To assess the extent of liver disease at the start of each treatment, a subgroup of rats were sacrificed after a two-week washout of DEN and the liver was harvested and processed for analysis. Masson's trichrome stains of liver sections from each animal were analyzed by a blinded pathologist. After 8 weeks and 12 weeks of DEN administration, no macroscopic findings were observed on the surface of the liver (FIG. 8A). However, microscopic examination revealed that the rats had early stages of liver fibrosis at 8 weeks which progressed to late fibrosis/early cirrhosis by 12 weeks. After 15 weeks of DEN administration, the rats had progressed to late stage cirrhosis which could be observed macroscopically on the surface of the liver (FIG. 8A) as well as microscopically. Rats receiving vehicle or gefitinib were sacrificed at 18 weeks after a two-week washout of DEN. The liver was harvested and processed for analysis. Masson's trichrome stains of liver sections from each animal were scored by a blinded pathologist by the method of Ishak. Gefitinib inhibited the progression of liver fibrosis/pre-cirrhosis when it was administered after either 8 or 12 weeks, but not after 15 weeks (FIG. 8B). These data suggest that the effects of gefitinib on liver disease progression only occur during fibrosis and pre-cirrhosis. Once the disease has progressed to late stage cirrhosis, e.g., macroscopic cirrhosis, it can no longer be prevented.

Example 7

To investigate erlotinib as a treatment and preventive strategy for liver fibrogenesis, male Wistar rats are given a weekly intraperitoneal injection of 50 mg/kg DEN to induce cirrhosis and HCC (Lee et al., Korean J Hepatol 13:70-80, 2007). Erlotinib is administered by intraperitoneal injection daily (5× a week) during weeks 6-12, 12-18, or 10-12, at a dose of either 2 mg/kg, which is equivalent to chemotherapeutic dosing regimens in humans, or 0.5 mg/kg, which as described above inhibited tumor formation by 49% when administered at weeks 12-18.

Liver function tests are performed as described above in Example 3 to evaluate hepatotoxicity and liver failure. In addition, histology is performed to evaluate fibrogenesis. The results are expected to demonstrate a reduction in fibrogenesis in the animals treated with erlotinib.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing liver fibrosis or pre-cirrhosis in a subject, the method comprising:
    selecting a subject on the basis that they have, or are at risk of developing, liver fibrosis or pre-cirrhosis, wherein pre-cirrhosis is a condition prior to development of macronodular cirrhosis; and
    administering to the subject a therapeutically effective amount of an epidermal growth factor receptor (EGFR) inhibitor, wherein the EGFR inhibitor is a quinazoline, thereby reducing liver fibrosis or pre-cirrhosis in the subject.

2. The method of claim 1, wherein selecting a subject comprises detecting the presence of liver fibrosis or pre-cirrhosis.

3. The method of claim 2, wherein detecting the presence of liver fibrosis comprises performing one or more tests selected from the group consisting of a liver biopsy, a blood test, and radiological imaging of the liver, and wherein the results of the test indicate that the subject has fibrosis, but does not have macronodular cirrhosis or hepatocellular carcinoma.

4. The method of claim 2, wherein detecting the presence of pre-cirrhosis comprises performing one or more tests selected from the group consisting of a liver biopsy, a blood test, and radiological imaging of the liver, and wherein the results of the test indicate that the subject has pre-cirrhosis, but does not have macronodular cirrhosis or hepatocellular carcinoma.

5. The method of claim 3, wherein the blood test comprises assaying levels of one or more of aspartate aminotransferase, alanine aminotransferase, bilirubin, glucose, or hyaluronate.

6. The method of claim 4, wherein the blood test comprises assaying levels of one or more of aspartate aminotransferase, alanine aminotransferase, bilirubin, glucose, or hyaluronate.

7. The method of claim 1, wherein the EGFR inhibitor is erlotinib.

8. The method of claim 1, wherein the EGFR inhibitor is administered orally, intravenously, or by injection.

9. The method of claim 1, wherein the amount of EGFR inhibitor administered comprises 0.1 to 3.0 milligram per kilogram body weight.

10. The method of claim 9, wherein the amount of EGFR inhibitor administered is about 0.5 milligram per kilogram body weight.

11. The method of claim 1, wherein the subject is a mammal.

12. The method of claim 1, wherein the subject is a human.

13. The method of claim 1, further comprising detecting an effect of EGFR inhibition on liver fibrosis or pre-cirrhosis in the subject by measuring one or more of aspartate aminotransferase, alanine aminotransferase, bilirubin, hyaluronate or glucose in the subject.

* * * * *